(12) United States Patent
Kirn

(10) Patent No.: US 9,713,691 B2
(45) Date of Patent: Jul. 25, 2017

(54) DEVICE FOR SECURING AN ORAL TUBE IN A PATIENT

(75) Inventor: David S. Kirn, Lexington, KY (US)

(73) Assignee: KIRN MEDICAL DESIGN LLC, Lexington, KY (US)

( * ) Notice: Subject to any disclaimer, the term of this patent is extended or adjusted under 35 U.S.C. 154(b) by 560 days.

(21) Appl. No.: 13/704,478

(22) PCT Filed: Jun. 17, 2011

(86) PCT No.: PCT/US2011/040854
§ 371 (c)(1),
(2), (4) Date: Dec. 14, 2012

(87) PCT Pub. No.: WO2011/159997
PCT Pub. Date: Dec. 22, 2011

(65) Prior Publication Data
US 2013/0087152 A1   Apr. 11, 2013

Related U.S. Application Data

(60) Provisional application No. 61/355,908, filed on Jun. 17, 2010.

(51) Int. Cl.
*A61M 16/04* (2006.01)
*A61M 25/02* (2006.01)

(52) U.S. Cl.
CPC .... *A61M 16/0497* (2013.01); *A61M 16/0488* (2013.01); *A61M 16/0493* (2014.02);
(Continued)

(58) Field of Classification Search
CPC .............. A61M 16/04; A61M 16/0461; A61M 16/0465; A61M 16/0497; A61M 16/0488;
(Continued)

(56) References Cited

U.S. PATENT DOCUMENTS 3,927,676 A   12/1975  Schultz
3,946,742 A    3/1976  Eross
(Continued)

FOREIGN PATENT DOCUMENTS

BE        1014139 A3      5/2003
WO       W099/65553 A1   12/1999
WO    WO 2010033109 A1 *  3/2010

OTHER PUBLICATIONS

Anderson et al. The nasal loop provides an alternative to percutaneous endoscopic gastrostomy in high-risk dysphagic stroke patients. Clin Nutrition (2004) 23, 501-506.*
(Continued)

*Primary Examiner* — Kathryn E Ditmer
(74) *Attorney, Agent, or Firm* — King & Schickli, PLLC

(57) ABSTRACT

A device for securing an oral tube, such as an endotracheal tube, positioned in a patient's trachea includes a support surface, such as an open channel, for supporting the tube. First and second arms extend outwardly from the open channel. The first and second arms form an arch having first and second ends. Bite blocks are provided adjacent the first and second arch ends for contacting the patient's teeth or gums, and a receiver for securing the tube against the support surface is likewise provided. A flexible member having first and second ends for looping around the patient's nasal septum is likewise provided. At least one of the ends of the flexible member is received in a retainer and assists in securing the device in position.

16 Claims, 9 Drawing Sheets

(52) U.S. Cl.
CPC ....... *A61M 25/02* (2013.01); *A61M 2025/022* (2013.01); *A61M 2025/0226* (2013.01); *A61M 2210/0618* (2013.01); *A61M 2210/0625* (2013.01)

(58) Field of Classification Search
CPC .......... A61M 16/0666; A61M 16/0683; A61M 25/02; A61F 2025/022; A61F 2025/0226; A61F 2025/024; Y10S 128/26
USPC ........................ 128/207.14, 207.17; 604/174
See application file for complete search history.

(56) References Cited

U.S. PATENT DOCUMENTS

| | | | |
|---|---|---|---|
| 3,972,321 A | 8/1976 | Proctor | |
| 3,976,080 A | 8/1976 | Bornhorst et al. | |
| 3,993,081 A | 11/1976 | Cussell | |
| 4,142,527 A | 3/1979 | Garcia | |
| 4,270,529 A | 6/1981 | Muto | |
| 4,331,143 A | 5/1982 | Foster | |
| 4,351,331 A | 9/1982 | Gereg | |
| 4,378,012 A | 3/1983 | Brown | |
| 4,392,857 A | 7/1983 | Beran | |
| 4,449,527 A | 5/1984 | Hinton | |
| 4,520,813 A | 6/1985 | Young | |
| 4,530,354 A | 7/1985 | Froilan | |
| 4,537,192 A | 8/1985 | Foster | |
| 4,548,200 A | 10/1985 | Wapner | |
| 4,634,425 A * | 1/1987 | Meer | 604/533 |
| 4,658,814 A | 4/1987 | Anderson | |
| 4,683,882 A | 8/1987 | Laird | |
| 4,744,358 A | 5/1988 | McGinnis | |
| 4,774,944 A | 10/1988 | Mischinski | |
| 4,832,019 A | 5/1989 | Weinstein et al. | |
| 4,906,234 A | 3/1990 | Voychehovski | |
| 5,009,227 A | 4/1991 | Nieuwstad | |
| 5,038,778 A | 8/1991 | Lott | |
| 5,042,477 A | 8/1991 | Lewis | |
| 5,069,206 A * | 12/1991 | Crosbie | 128/207.17 |
| 5,076,269 A * | 12/1991 | Austin | 128/207.17 |
| 5,123,410 A | 6/1992 | Greene et al. | |
| 5,146,913 A | 9/1992 | Khorsandian et al. | |
| 5,185,005 A | 2/1993 | Ballantyne | |
| 5,305,742 A | 4/1994 | Styers et al. | |
| 5,306,233 A | 4/1994 | Glover | |
| 5,320,097 A | 6/1994 | Clemens et al. | |
| 5,345,931 A | 9/1994 | Battaglia, Jr. | |
| 5,368,024 A | 11/1994 | Jones | |
| 5,383,451 A | 1/1995 | DeIulio | |
| 5,386,821 A | 2/1995 | Poterack | |
| 5,398,679 A | 3/1995 | Freed | |
| 5,402,776 A | 4/1995 | Islava | |
| 5,411,484 A | 5/1995 | Shattuck | |
| 5,437,273 A | 8/1995 | Bates et al. | |
| 5,448,985 A | 9/1995 | Byrd | |
| 5,490,504 A | 2/1996 | Vrona et al. | |
| 5,513,633 A | 5/1996 | Islava | |
| 5,555,881 A | 9/1996 | Rogers et al. | |
| 5,558,090 A | 9/1996 | James | |
| 5,626,128 A | 5/1997 | Bradley et al. | |
| 5,626,565 A | 5/1997 | Landis et al. | |
| 5,638,814 A | 6/1997 | Byrd | |
| 5,653,228 A | 8/1997 | Byrd | |
| 5,653,232 A | 8/1997 | Rogers et al. | |
| 5,699,787 A * | 12/1997 | Thompson | 128/200.26 |
| 5,803,079 A | 9/1998 | Rogers et al. | |
| 5,806,516 A | 9/1998 | Beattie | |
| 5,829,430 A | 11/1998 | Islava | |
| 5,868,132 A * | 2/1999 | Winthrop et al. | 128/207.14 |
| 5,894,840 A | 4/1999 | King | |
| 5,934,276 A | 8/1999 | Fabro et al. | |
| 5,996,581 A | 12/1999 | Duch | |
| 6,050,263 A | 4/2000 | Choksi et al. | |
| 6,067,985 A | 5/2000 | Islava | |
| D434,496 S | 11/2000 | Choksi et al. | |
| 6,336,457 B1 | 1/2002 | Hudson et al. | |
| 6,408,850 B1 * | 6/2002 | Sudge | 128/207.17 |
| 6,464,668 B1 | 10/2002 | Pace | |
| 6,526,978 B2 | 3/2003 | Dominguez | |
| 6,561,192 B2 | 5/2003 | Palmer | |
| 6,631,715 B2 | 10/2003 | Kirn | |
| 6,675,808 B2 | 1/2004 | Karasic | |
| 6,810,878 B2 | 11/2004 | Palmer | |
| 7,017,579 B2 | 3/2006 | Palmer | |
| 7,063,088 B1 | 6/2006 | Christopher | |
| 2004/0069309 A1 * | 4/2004 | Kirn | 128/207.18 |
| 2005/0236001 A1 * | 10/2005 | Williams | 128/207.18 |
| 2007/0135770 A1 | 6/2007 | Hunt et al. | |
| 2010/0083970 A1 | 4/2010 | Beely et al. | |
| 2010/0180900 A1 * | 7/2010 | Talsma et al. | 128/207.14 |

OTHER PUBLICATIONS

Gray et al. Intra-operative endotracheal tube stabilization for facial burns. Burns (2010) 36, 572-575.*
Rooney et al. Use of the nasal bridle to secure fixation of an endotracheal tube in a child with facial blistering secondary to toxic epidermal necrolysis. Burns (2010) 36, e143-e144.*
International Search Report for International application No. PCT/US2011/040854 dated Sep. 20, 2011.

* cited by examiner

DEVICE FOR SECURING AN ORAL TUBE IN A PATIENT

This application is the national stage of international patent application no. PCT/US2011/040854 filed on Jun. 17, 2011, which in turn claims priority from U.S. Provisional Patent Application Ser. No. 61/355,908 filed on Jun. 17, 2010, the disclosures of each of which are incorporated herein by reference in their entirety.

FIELD OF THE INVENTION

The present invention relates generally to an apparatus for securing oral tubes; and more particularly to an apparatus and method for securing an oral tube once the tube is positioned within a patient.

BACKGROUND OF THE INVENTION

Oral tubes, such as endotracheal (ET) tubes, are routinely used in the practice of medicine. ET tubes, for example, typically extend into a patient's trachea in order to provide a stable airway and permit connection to a mechanical ventilation system. ET tubes can also be used in the delivery of medicines in certain circumstances. In practice, ET tubes are inserted through a patient's mouth and into the trachea to ensure that the airway is not closed off and that air is able to reach the lungs. Once placed in a patient's trachea, the ET tube must be secured in order to prevent potentially harmful movement of the tube.

Many different devices and methods have been used to secure oral tubes such as ET tubes once positioned within a patient. The most commonly employed method is simply to use an adhesive tape placed across the tube and adhering to the patient's facial skin. A review of the noted devices and methods reveals three broad categories of oral tube securing or anchoring devices. The first category involves the use of one or more straps which typically extend around a patient's head, neck, or ears. The second category, discussed briefly above, involves the use of tapes or adhesives to secure the tube, and the third category relies on a patient's teeth for fixation of the tube in position.

A seeming majority of the prior art patent literature surrounds the use of straps which are passed around the patients head, neck, or ears and are attached to a clamp to secure the tube in position. Examples of these types of devices and methods are shown in U.S. Pat. No. 3,946,742 to Eross and U.S. Pat. No. 5,490,504 to Vrona et al. which each disclose devices that utilizes a clamp and a strap to secure an ET tube. Examples of similar devices and methods which combine a strap with a tape or adhesive component are shown in U.S. Pat. No. 3,927,676 to Schultz, U.S. Pat. No. 5,306,233 to Glover, and U.S. Pat. No. 5,448,985 to Byrd. Still other examples of devices and methods which incorporate a clamp, a bite block, and a strap are shown in U.S. Pat. No. 4,351,331 to Gereg and U.S. Pat. No. 5,894, 840 to King.

Although each of these exemplary devices appears effective in attaining the primary goal of securing the tube, each has its drawbacks and side effects which affect the patient. For example, devices which utilize straps can be difficult and time consuming to install and are generally uncomfortable for the patient. Even more, straps can abrade or damage the patient's skin over time. This is particularly true when straps are used in the care of burn patients whose skin has already been damaged.

Additional prior art patent literature can be found that illustrates the utilization of adhesives to secure tubes. Examples of these second category devices are illustrated in U.S. Pat. No. 3,993,081 to Cussell and U.S. Pat. No. 5,868,132 to Wintrhop et al. and each relies solely on the adherence of an adhesive to anchor the tube. Although each of these exemplary devices appears effective in attaining the primary goal of securing the tube, each has its drawbacks and side effects which affect the patient. All adhesives which are suitable for use in a medical setting, for example, have a tendency to lose adhesion over time due to degradation of the adhesive material and skin oil among other factors. Similarly, the patient can react to or be allergic to the adhesives leading to skin damage. This is particularly the case in pediatric patients who are prone to the development of adhesive tape allergies.

Last, even more patent literature can be found that illustrates the utilization of the patient's teeth to secure oral tubes. One example of such a third category device is illustrated in U.S. Pat. No. 6,675,808 to Karasic. Although the exemplary device appears effective in attaining the primary goal of securing the ET tube, it has its drawbacks and side effects which affect the patient. For example, devices which utilize the patient's teeth require that the patient have teeth. Even more, such devices can result in damage or injury to the patient's teeth.

Anchoring of nasal tubes, including nasotracheal tubes can be achieved by placing a loop of flexible material (e.g., cotton umbilical tape) around the patient's nasal septum and vomer bone as provided in U.S. Pat. No. 6,631,715 and U.S. Pat. No. 6,837,237 each issued to the present applicant. This concept allows for the securement of nasal tubes without the use of adhesive tape or the placement of straps around the patient's head, and can be accomplished in a rapid, safe, and convenient manner.

Accordingly, a need exists for a device and method capable of quickly, comfortably, and safely securing an oral tube once the tube is positioned within a patient. In addition, the apparatus would preferably not require the utilization of adhesive tapes or straps positioned around the patient's head, or rely on the patient having teeth in order to secure the tube. All of the said features are provided by the following invention. Naturally, any improvements along such lines should contemplate good engineering practices, such as simplicity, ease of implementation, unobtrusiveness, stability, etc.

SUMMARY OF THE INVENTION

The present invention meets these needs by providing a device for securing an oral tube, such as an endotracheal tube, positioned in a patient's trachea. The device comprises an open channel for supporting the tube and first and second arms extending outwardly from the open channel. The first and second arms form an arch having first and second ends. Bite blocks are provided adjacent the first and second arch ends for contacting the patient's teeth or gums, and a receiver for securing the tube against the open channel is likewise provided.

In accordance with a first aspect of the present invention, the device for securing the oral tube positioned in a patient's trachea may further include a flexible member having first and second ends for looping around the patient's nasal septum, and a retainer for receiving at least one of the first and second ends of the flexible member for securing the device in position.

In another aspect of the invention, the receiver includes first and second pivotally connected portions forming a channel for the tube. The portions form a locking member which allows the diameter of the channel to vary dependent upon the size of the tube. In one embodiment, the locking member is a ratchet type licking mechanism.

In yet another aspect of the invention, the device for securing the tube positioned in a patient's trachea comprises a tube supporting surface and first and second arms extending outwardly from the supporting surface. The first and second arms form an arch contacting the patient's teeth or gums. A flexible member having first and second ends loops around the patient's septum and a retainer receives at least one of the flexible member ends for securing the device in position.

Additional advantages and other novel features of the invention will be set forth in part in the description that follows and in part will become apparent to those skilled in the art upon examination of the following or may be learned with the practice of the invention. The objects and advantages of the invention may be realized and attained by means of the instrumentalities and combinations particularly pointed out in the appended claims.

BRIEF DESCRIPTION OF THE DRAWINGS

The accompanying drawings incorporated in and forming a part of the specification, illustrate several aspects of the present invention, and together with the description serve to explain the principles of the invention. In the drawings.

Reference will now be made in detail to the present embodiment of the invention, an example of which is illustrated in the accompanying drawings.

DETAILED DESCRIPTION OF THE PREFERRED EMBODIMENT

Figure 1:
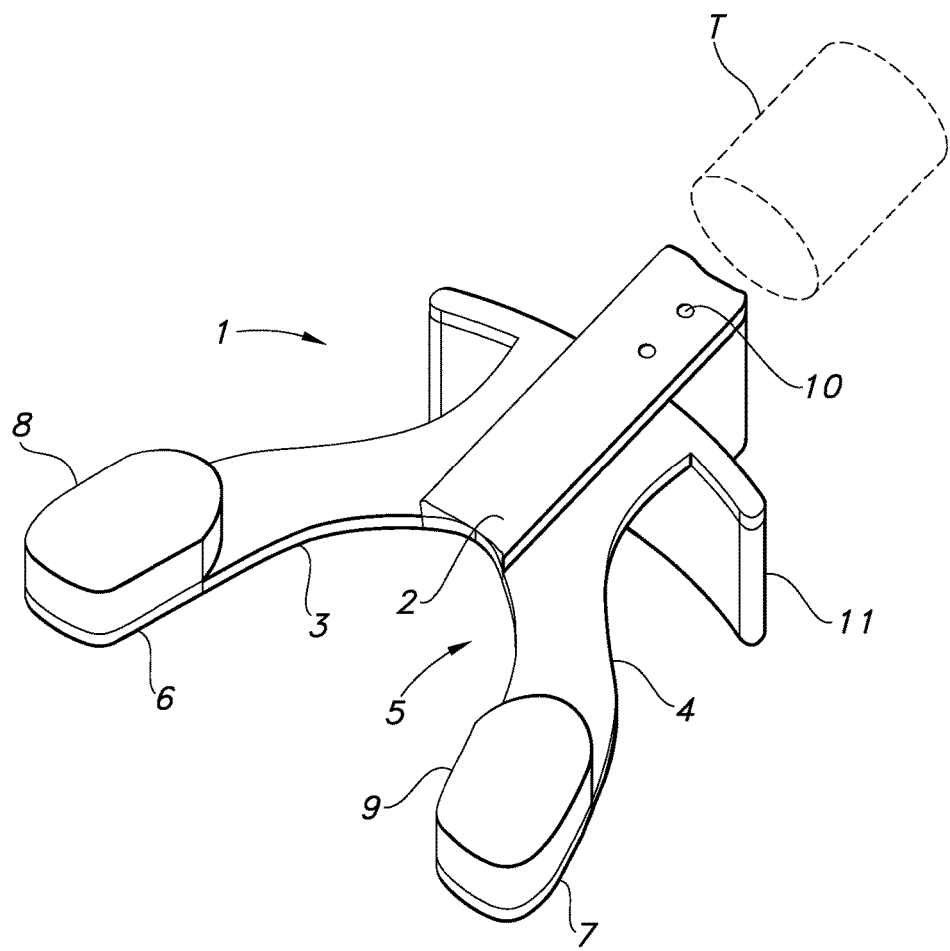
FIG. 1 is a partial perspective view of the bottom side of a device for securing an endotracheal tube positioned in a patient's trachea.

With reference to the perspective view of FIG. 1, there is shown an embodiment of a device 1 for securing an oral tube which in this instance is an ET tube (T) positioned in a patient's trachea. The device is preferably semi-rigid and molded of a polymer or other like materials. In use, the device is partially inserted into a patient's mouth. Necessarily, a portion of the device 1 extends outside of the patient's mouth. As is readily apparent, the portion of the device 1 inside of the patient's mouth generally conforms to the shape of the dental arch.

The device 1 includes a tube supporting surface 2, such as an open channel, for supporting the ET tube (T), a first arm 3 extending outwardly from the supporting surface or open channel and a second arm 4 extending outwardly from the open channel. The first and second arms 3, 4 generally form an arch 5 as suggested above having first and second ends 6, 7. A first bite block 8 adjacent the first arch end 6 and a second bite block 9 adjacent the second arch end 7 are provided for contacting the patient's teeth or gums once inserted in order to limit lateral movement of the device 1.

In an alternate embodiment not shown in the present drawings, the space between the first and second arms 3, 4 which form the arch 5 could be filled in and generally conform to the curve of the hard and/or soft palate. This would be similar in shape to a retainer provide by an orthodontist. In this configuration, lateral motion of the device 1 would be further limited through contact with the palate. In yet another embodiment, an extension of material along the first and second arms 3, 4 extending upward and conforming to an exterior (buccal) aspect of the dental arch would similarly serve to limit lateral motion of the device 1. In addition, the tube supporting surface 2 could take most any shape.

In the present embodiment, the open channel 2 may include a plurality of protrusions 10 to reduce and/or eliminate slipping of the ET tube (T) along the open channel. The protrusions 10 could be integrally formed and take any number of shapes including cylindrical or conical, for example, or merely be semi-spheres or bumps along the open channel 2.

The device 1 may further include a bumper 11 as shown in FIG. 1. The bumper 11 may comfortably rest against a patient's mouth or lips when the device is positioned within the patient's mouth. The bumper 11 is generally anatomically curved and rests along an external aspect of the patient's upper lip thereby distributing any pressure on the lip over a large surface area in order to avoid pressure related injury to the upper lip. In an alternate embodiment, this area may have a soft and/or padded material attached, such as foam, to contact the upper lip, or this area could also have an adhesive to attach to the lip. The size and shape of the bumper 11 can also be modified into a variety of configurations to accommodate clinical need or the patient's anatomy, or it could be eliminated altogether.

Figure 2:
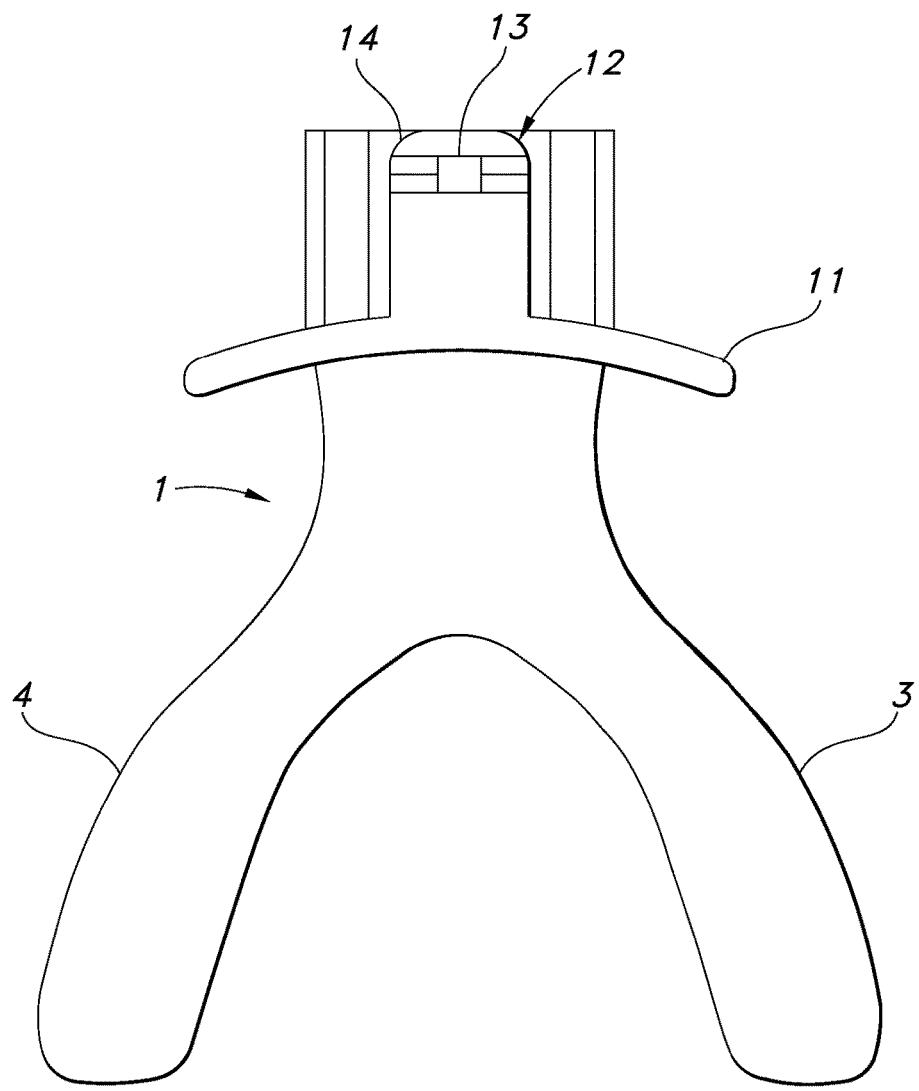
FIG. 2 is a top view of the device.

With reference to the top view of FIG. 2, a retainer 12 is shown adjacent and above the open channel 2 and bumper 11. The retainer 12 is designed to receive and secure first and second ends of a flexible member 16 (shown in FIG. 7) for securing the device 1 in position. The retainer 12 includes a hinge 13 for opening and closing a clip 14 to secure the flexible member 16 in position around the patient's nasal septum as will be described in more detail below. In this embodiment, the hinge 13 is integrally molded forming a living hinge and the clip 14 snaps closed to secure the flexible member 16 in position.

The looping of the flexible member 16 around the patient's nasal septum forms a nasal loop. Thus, a fixed anchor point is established by the connection of the device 1 with the nasal loop formed by the flexible member 16. A second point of fixation is established by the connection of the device 1 with the ET tube (T). Some degree of pivot is possible around the fulcrum at the attachment point of the nasal loop. However, rotation about this fulcrum is limited by the close proximity of the maxillary and mandibular dental arches and the bite blocks 8, 9.

Figure 3:
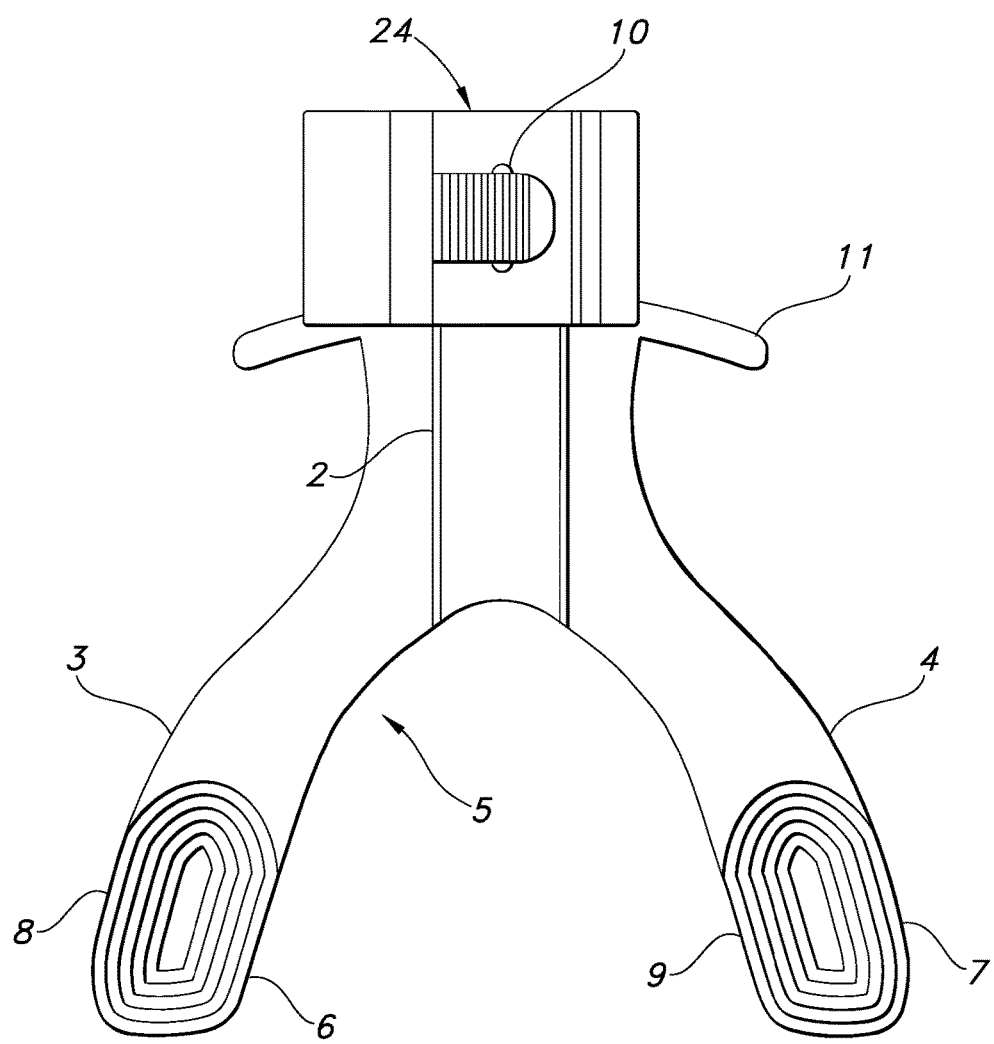
FIG. 3 is a bottom view of the device including a receiver for receiving and securing the endotracheal tube.

As shown in FIG. 3, the device 1 includes a receiver 24 which will be described in greater detail below for securing the ET tube (T) therein. In addition, exemplary conically shaped protrusions 10 are also shown positioned along the open channel 2. As indicated earlier and in accordance with the broadest teachings of the present invention, the protrusions can be made in varying shapes and any number of protrusions can be utilized and placed along the open channel. Placement of the protrusions along the open channel can be random or ordered to accommodate the desired effect of limiting or preventing slippage of the ET tube (T) when positioned adjacent the open channel 2.

Figure 4:
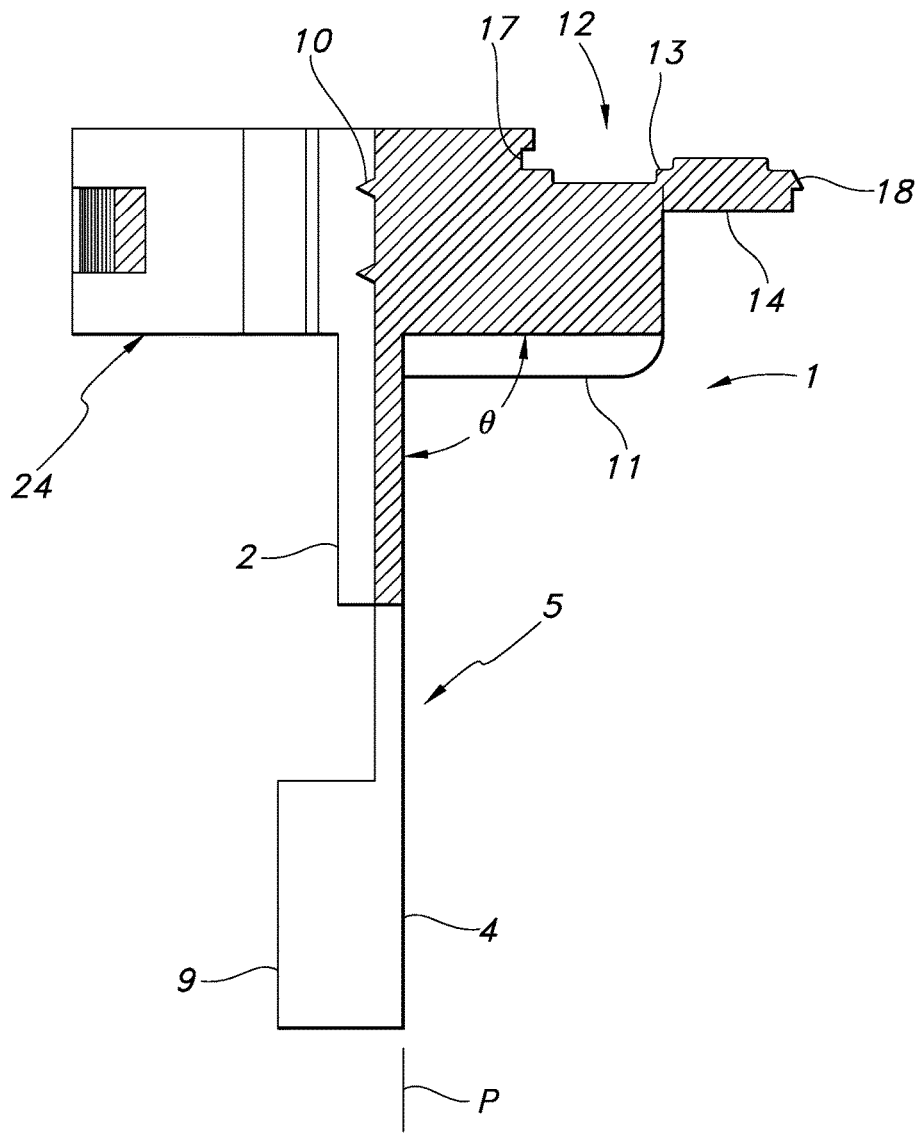
FIG. 4 is a cross-sectional view at the mid-point of the device illustrating an open retainer for receiving first and second ends of a flexible member for securing the device in position, and an open receiver for receiving a endotracheal tube.
Figure 5:
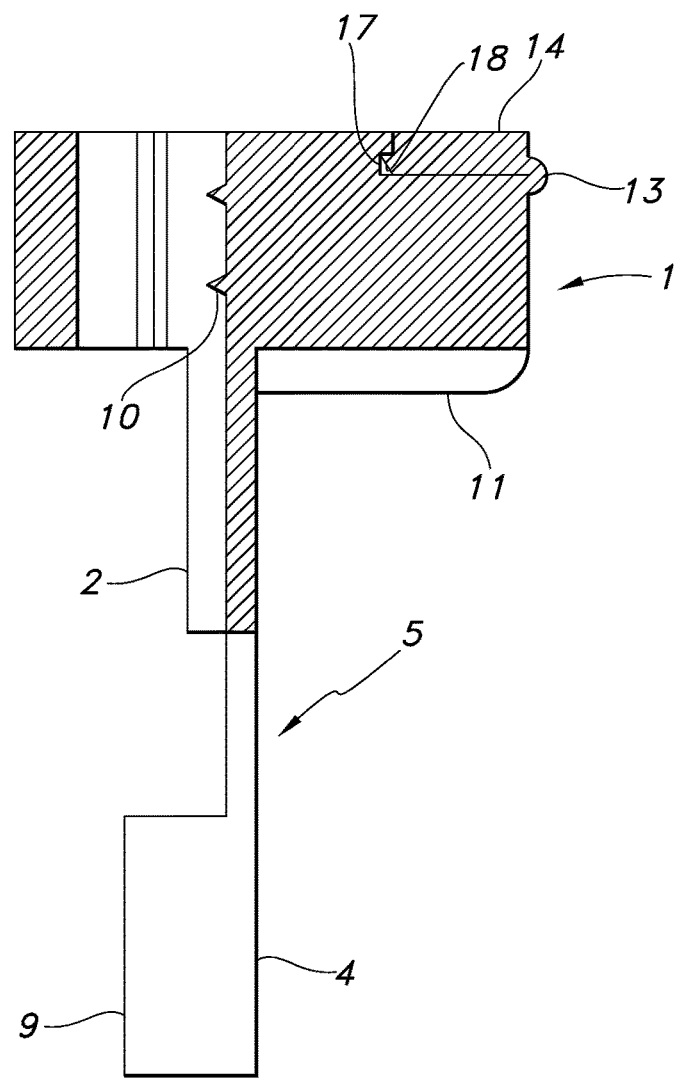
FIG. 5 is a cross-sectional view at the mid-point of the device illustrating the retainer and receiver in closed positions.

FIGS. 4 and 5 are cross-sectional views at the midpoint of the device 1 which show retainer 12 and receiver 24 in open and closed positions respectively. The integrally molded living hinge 13 allows for the opening and closing of retainer 12. In the present embodiment, a snapping mechanism is likewise integrally molded and provides a locking feature when the retainer 12 is in the closed position. Specifically, a tapered edge 18 extends from an end of a retainer clip 14. A void 17 is formed in the device 1 for receiving the tapered edge 18 in the closed position shown in FIG. 5. The receiver 24 is likewise shown in open and closed position for receiving the ET tube (T) and securing the tube in the open channel 2. Details of the receiver 24 are described below.

As further shown in FIGS. 4 and 5 and indicated in FIG. 4, bumper 11 is formed at an angle θ to a plane (P) generally formed by first and second arms 3, 4 and open channel 2. In this embodiment, the angle θ is generally 90 degrees. In alternate embodiments, however, the angle θ formed between the bumper 11 and plane (P) may be more acute to facilitate closer conformity to human anatomy thereby providing a more comfortable feel for the patient.

Figure 5A:
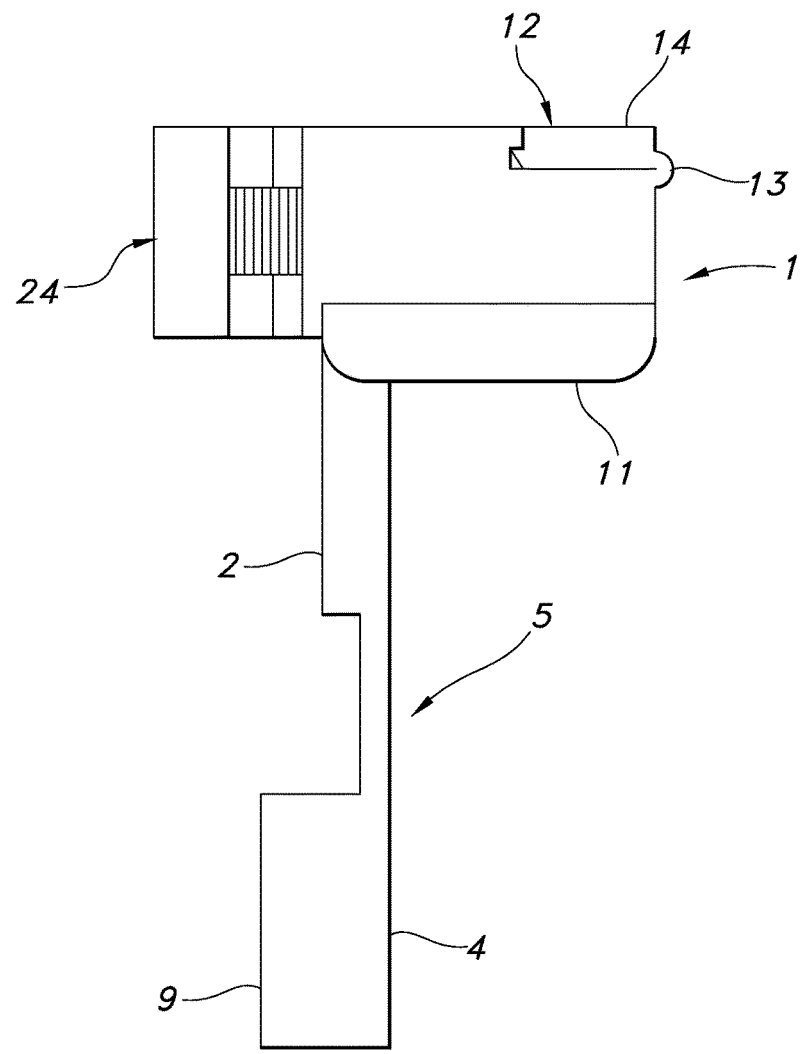
FIG. 5A is a side view of the device illustrating the retainer and receiver in closed positions.

FIG. 5a is a side view of the device 1 illustrating the retainer 12 and receiver 24 in the closed positions.

Figure 6:
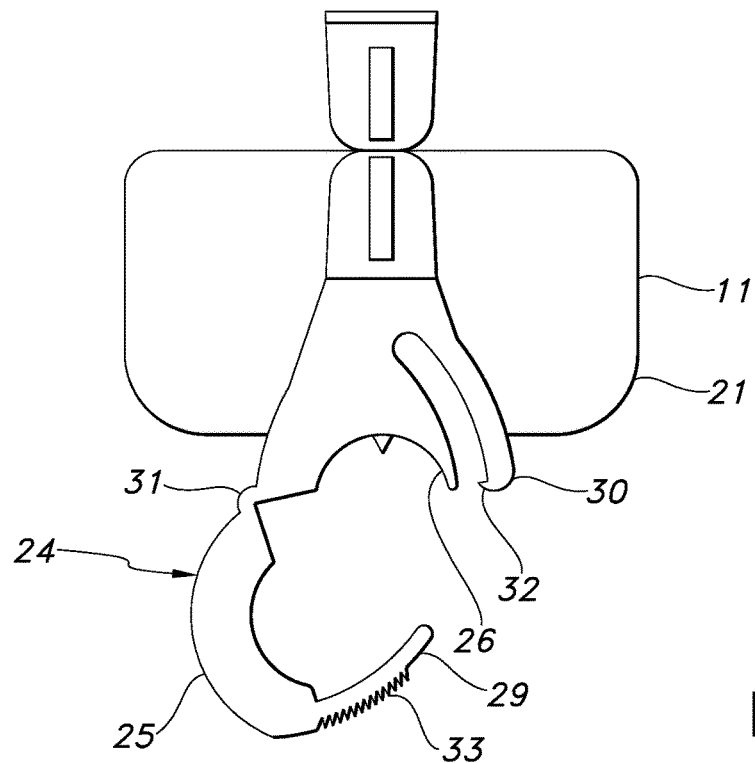
FIG. 6 is an end view of an anterior aspect of the device illustrating the retainer and receiver in open positions.
Figure 6A:
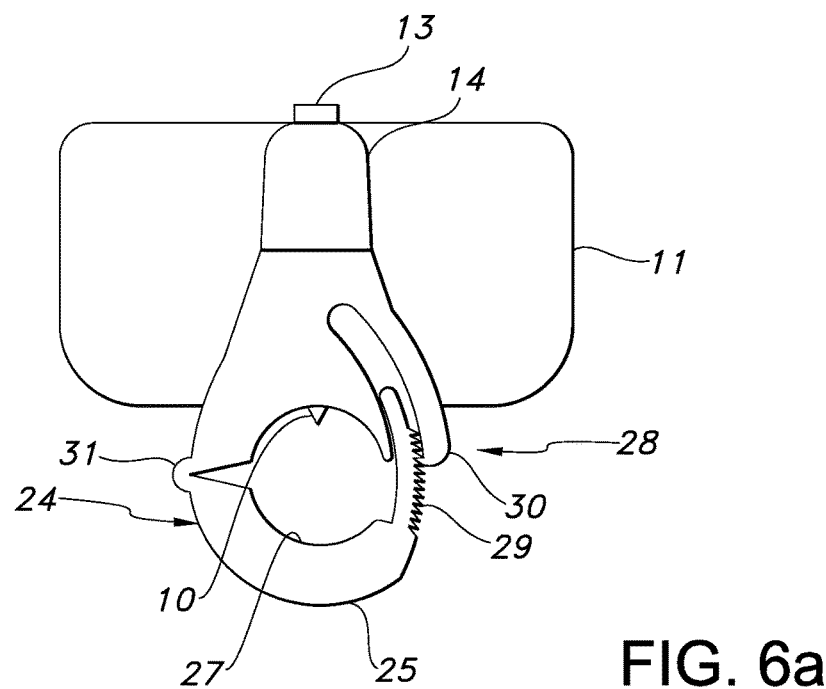
FIG. 6A is an end view of an anterior aspect of the device illustrating the retainer and receiver in closed positions.

With reference to FIGS. 6 and 6A, an end view of the device 1 is shown illustrating an alternate and presently preferred receiver 24 in opened and closed positions for receiving the ET tube (T)(not shown). The receiver 24 includes first and second pivotally connected portions 25, 26 forming a channel 27 therein for receiving a portion of the ET tube (T) and securing the tube in the receiver channel. In this embodiment, the hinge 31 is integrally molded forming a living hinge. The receiver channel 27, formed when pivotally connected portion 25 is moved to a closed position, generally forms an extension of or a portion of the open channel 2 for supporting the ET tube (T). Once the ET tube (T) is inserted through the receiver 24, the first pivotally connected 25 portion may be manually closed thereby securing the tube against protrusions 10 and in a secure position.

A locking mechanism 28 is formed in the first and second pivotally connected portions 25, 26. Specifically, the locking mechanism 28 includes male and female parts 29, 30, respectively, which are designed to incrementally close the pivotally connected portions 25, 26. In the present embodiment, the male and female parts 29, form a ratchet type locking mechanism. The female part 30 includes a cavity for receiving the male part 29 in the closed position. A retaining tang 32 is formed on female part 30 for mating with the male part 29 and specifically, a row of teeth 33 formed on the male part. The tang 32 works in concert with the teeth 33 to provide the ratchet and incremental locking capabilities. As shown in the closed position in FIG. 6A, the diameter of the receiver channel 27 is adjustable dependent upon insertion of the male part 29 into female part 30. In this manner, tubes of varying diameters can be secured without occluding the tube with the locking mechanism 28 being adjusted to secure the tube in a firm but gentle manner.

Curved edges 21 of bumper 11 are also shown in FIG. 6. All surfaces of the device 1 which might impinge upon the patient at any contact point are curved or chamfered to minimize the risk of pressure injury. In an alternate embodiment, the size of bumper 11 could be minimized or this component could be eliminated altogether.

Figure 7:
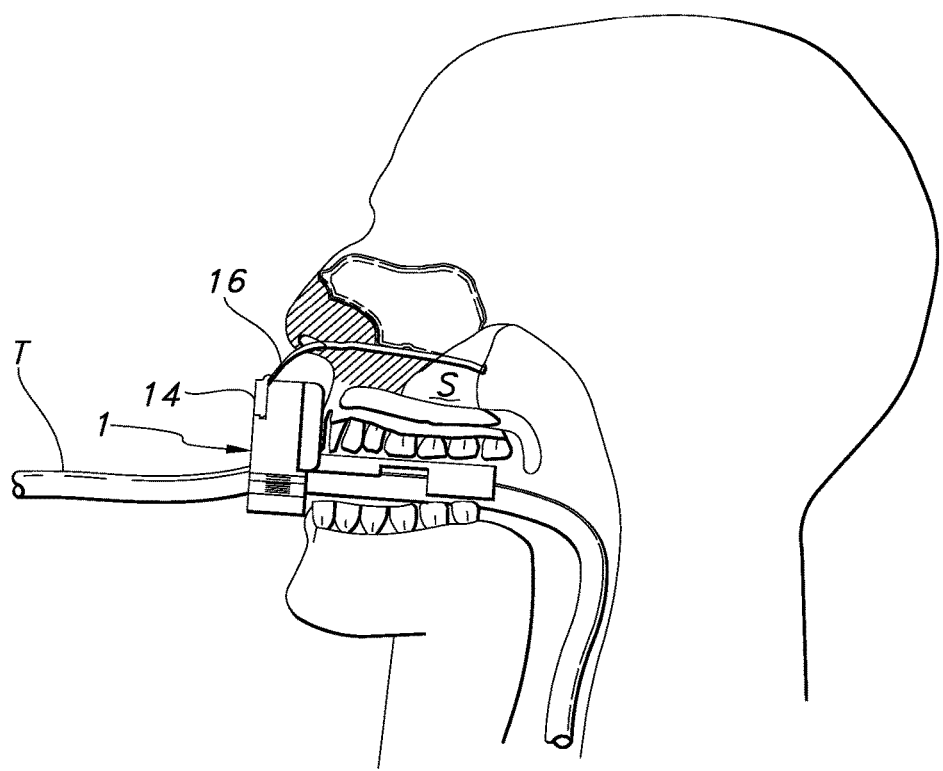
FIG. 7 is a cross-sectional view showing a flexible member positioned around a patient's septum to secure the device which is positioned in the patient's mouth and securing an inserted endotracheal tube positioned in the patient's trachea.

As shown in FIG. 7, the anchoring device 1 is positioned in a patient's mouth for securing an inserted ET tube (T) positioned in the patient's trachea. The flexible member 16 is also shown positioned around the patient's septum (S) to secure the device 1 in position. The retainer 12 used to secure the first and second ends of the flexible member 16 is positioned to substantially limit contact between the flexible member 16 and the patient's nares when flexible member is in position looped around the patient's septum (S). The ET tube (T), flexible member 16 or nasal loop, and device 1 may be placed in the patient in any sequence. For example, the ET tube (T) could be positioned within the patient's trachea followed by insertion of the flexible member 16 through the nare and around the septum. Once these are in position, the device 1 could be positioned in the patient's mouth and the ET tube (T) and flexible member secured to the device 1 at that time.

Figure 8:
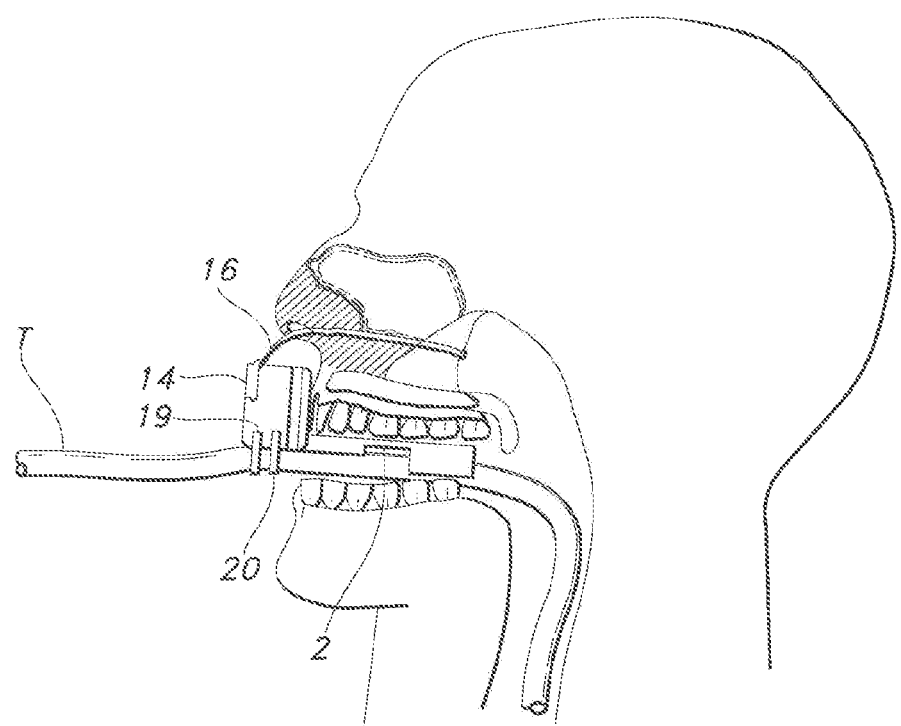
FIG. 8 is a cross-sectional view of an alternate embodiment showing a flexible member positioned around a patient's septum to secure the device.

In the present embodiment, the open channel 2 opens downwardly and the ET tube (T) rests on the open channel. The ET tube (T) is secured to open channel 2 by retainer 24 which receives the ET tube (T) and secures it against the channel. As described above, other means for securing the ET tube (T) against the open channel 2 in accordance with the broad teachings of the present invention are available and are considered to be within the broad scope of this invention. FIG. 8, for example, illustrates apertures 19 positioned beneath and adjacent to open channel 2. In this alternate embodiment, the apertures 19 receive means 20 for securing the ET tube (T) against the open channel. In accordance with the broad teachings of the present invention, the ET tube (T) may be secured by means of zip ties 20, string, or other equivalent binding method.

As also shown in FIG. 7, bite block 8 provides a comfortable surface for the patient to bite down on the device 1. This increases the comfort level experienced by the patient and helps maintain the device 1 in a secure and proper position relative the patient's dentition. The relationship between them serves to prevent cranial and caudal motion about the fulcrum point where nasal loop 16 connects to the device. Even with the patient's mouth open, the size of bite blocks 8, 9 will allow it to contact the mandibular dentition before there is enough motion of the ET tube (T) to displace it. The ends of nasal loop 16 may also be tied together to provide further security against slipping through retainer 12.

Similarly, bite blocks 8, 9 prevent full mouth closing thereby keeping the patient from occluding the ET tube (T) by biting on it. Further, the bite blocks 8, 9 decrease pivoting action of the device 1 by decreasing the arc of possible motion between the maxillary and madibular dental arch. An alternate embodiment would provide a suitable configuration of bite blocks 8, 9 that contact the gingivae of an edentulous or partially edentulous patient. In another alternate embodiment, an inflatable segment could be utilized for approximation to the dental arch or other intraoral structures.

The foregoing description of the preferred embodiment of the invention has been presented for purposes of illustration and description. It is not intended to be exhaustive or to limit the invention to the precise form disclosed. Obvious modifications or variations are possible in light of the above teachings. For example, different sizes of the device 1 could be created to accommodate patients with different sized lips, dental arches, and the use of different sized ET tubes (T). In particular, this would account for pediatric patients who may require an appropriately sized device 1. The present invention further allows for access to both the nose and the oral cavity for routine suctioning and hygiene needs. Additional fixation points may also be provided near the nasal aperture or on the upper lip segment for anchoring of nasal tubes or other oral tubes to the device 1.

The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

The invention claimed is:

1. A device for securing a tube positioned in a patient's trachea, comprising:
   a surface configured for positioning at least partially within the patient's mouth for supporting the tube;
   first and second arms extending outwardly from said tube support surface and forming an arch generally shaped to correspond to the patient's dental arch;
   a flexible member having first and second ends for looping around the patient's nasal septum; and
   a receiver for securing the tube against said tube support surface and for securing said flexible member in position looped around the patient's nasal septum.

2. The device for securing a tube positioned in a patient's trachea in claim 1, wherein said receiver includes first and second pivotally connected portions forming a channel for receiving a portion of the tube.

3. The device for securing a tube positioned in a patient's trachea in claim 2, wherein said tube support surface and said channel are contiguous.

4. The device for securing a tube positioned in a patient's trachea in claim 2, wherein said receiver includes a locking mechanism that allows a diameter of said channel to vary dependent upon the diameter of the tube.

5. The device for securing a tube positioned in a patient's trachea in claim 4, wherein said locking mechanism is a ratchet type locking mechanism.

6. The device for securing a tube positioned in a patient's trachea in claim 1, wherein said receiver includes a retainer for securing at least one of said first and second ends of said flexible member.

7. The device for securing a tube positioned in a patient's trachea in claim 6, wherein said retainer includes a clip for securing said at least one of said first and second ends of said flexible member.

8. The device for securing a tube positioned in a patient's trachea in claim 7, wherein said retainer includes a void for receiving a tapered end of said clip in a closed position.

9. The device for securing a tube positioned in a patient's trachea in claim 6, wherein said retainer is positioned to substantially limit contact between said flexible member and the patient's nares when said flexible member is in position looped around the patient's nasal septum.

10. The device for securing a tube positioned in a patient's trachea in claim 6, wherein said retainer is positioned a distance away from said tube support surface.

11. The device for securing a tube positioned in a patient's trachea in claim 10, wherein said retainer is positioned to substantially limit contact between said flexible member and the patient's nares when said flexible member is in position looped around the patient's nasal septum.

12. A device for securing a tube positioned in a patient's trachea, comprising:
   an open channel for supporting the tube, said open channel configured for positioning at least partially within the patient's mouth;
   first and second arms extending outwardly from said open channel and forming an arch configured such that a distal end of at least one of said first and second arms is adjacent a posterior tooth of the patient's teeth in use;
   a flexible member having first and second ends for looping around the patient's nasal septum;
   a receiver for securing the tube against said open channel; and
   a retainer for receiving at least one of said first and second ends of said flexible member to prevent removal of the tube when said tube is positioned in the patient's trachea.

13. The device for securing a tube positioned in a patient's trachea in claim 12, wherein said receiver includes a proximal end positioned adjacent said open channel and a distal end wherein said retainer is positioned.

14. The device for securing a tube positioned in a patient's trachea in claim 13, wherein said retainer includes a clip for securing said flexible member.

15. The device for securing a tube positioned in a patient's trachea in claim 12, wherein said retainer is positioned to substantially limit contact between said flexible member and the patient's nares in use.

16. The device for securing a tube positioned in a patient's trachea in claim 15, wherein said receiver includes a proximal end positioned adjacent said open channel and a distal end wherein said retainer is positioned.

* * * * *